(12) United States Patent
Van Huizen

(10) Patent No.: US 6,423,036 B1
(45) Date of Patent: Jul. 23, 2002

(54) CANNULA ANCHORING PORT

(75) Inventor: James Van Huizen, Virginia Beach, VA (US)

(73) Assignee: Gibbons Surgical Corporation, Virginia Beach, VA (US)

( * ) Notice: Subject to any disclaimer, the term of this patent is extended or adjusted under 35 U.S.C. 154(b) by 0 days.

(21) Appl. No.: 09/576,192

(22) Filed: May 23, 2000

Related U.S. Application Data

(60) Provisional application No. 60/137,862, filed on Jun. 7, 1999.

(51) Int. Cl.[7] .............................................. A61M 5/178
(52) U.S. Cl. ............................ 604/164.04; 604/164.01; 604/165.04; 604/174; 604/117
(58) Field of Search ............................. 604/93.01, 117, 604/158, 161, 164.01, 164.04, 165.01, 165.04, 174; 606/185

(56) References Cited

U.S. PATENT DOCUMENTS

| | | | |
|---|---|---|---|
| 4,645,492 A | * | 2/1987 | Weeks ........................ 604/174 |
| 4,650,473 A | | 3/1987 | Bartholomew et al. |
| 5,429,598 A | | 7/1995 | Waxman et al. |
| 5,683,378 A | | 11/1997 | Christy et al. |
| 5,971,958 A | * | 10/1999 | Zhang .................... 604/164.01 |
| 5,997,515 A | * | 12/1999 | de la Torre et al. ......... 604/246 |
| 6,228,063 B1 | * | 5/2001 | Aboul-Hosn ................. 604/174 |

* cited by examiner

*Primary Examiner*—Gregory Huson
*Assistant Examiner*—Tuan Nguyen
(74) *Attorney, Agent, or Firm*—Kimberly A. Chasteen, Esq.

(57) ABSTRACT

A port for anchoring a cannula is provided. The port consists of a sealing cap removably attached to a threaded cone top. The threaded cone top is threaded onto a cone section from which a plurality of arms extend. The arms include a system for retaining a thread such as a suture. For use in laparoscopic surgery, a cannula is inserted into the port, the port is secured to the cannula and the cannula/port assembly is secured to the surgical site using sutures and a suture retaining system on the port.

12 Claims, 6 Drawing Sheets

CANNULA ANCHORING PORT

This application claims priority from provisional application Ser. No. 60/137,862 filed Jun. 7, 1999.

BACKGROUND OF THE INVENTION

1. Technical Field of the Invention

The present invention relates generally to cannula ports, and more particularly to cannula ports which include an anchoring system.

2. Discussion of the Related Art

Laparoscopic surgery was developed in the 1960s as a diagnostic tool and has grown into a major surgical tool. The surgical procedure begins with the insertion of a special needle, the Verres needle, into, for example, the abdominal cavity. Gas, preferably $CO_2$, is inserted into the abdominal cavity through the needle until a pressure of approximately 12–15 mmHg is reached. A sharp metal trocar fitted with a cannula is then inserted through the cavity wall and held in place by means of a port. Generally more than one inserted cannula is required to introduce an imaging device, such as a telescope or camera, and surgical tools into the cavity to perform the required surgery.

Devices for performing this surgery are well known in the art. Previously, the cannula was held in place using sutures which were tied to arms on the cannula or on the port itself. This procedure is difficult and cumbersome to achieve during surgery and often results in broken sutures which must be replaced. The method securing the port to the cannula in prior art devices involves turning a screw against a metal band located inside of the port, also a cumbersome procedure during surgery. Additionally, the metal band is prone to losing its shape, requiring replacement.

It is accordingly an object of the present invention to provide a cannula port which includes a simple suture retention means.

It is another object of the present invention to provide a cannula port having a suture retention means which does not require tying of the suture.

It is another object of the present invention to provide a cannula port which is self tightening against a cannula.

It is another object of the present invention to provide a cannula port tightening means which provides a tight seal against a cannula.

It is yet another object of the present invention to accomplish the foregoing objects in a simple manner.

Additional objects and advantages of the present invention are apparent from the drawings and specification which follow.

SUMMARY OF THE INVENTION

According to the present invention, the foregoing and additional objects are obtained by providing a cannula port having a simplified suture retention means and simplified means for securing the port against the cannula. This port consists of a sealing cap which is removably attached to a threaded cone top, a cone which has an upper threaded section for receiving the threaded cone top and a lower conical section, and a plurality of arms extending from the cone, each arm including a means for retaining a thread such as a suture. The cone may have an upper section of vertical segments which are forced inward upon threading of the cone top onto the cone. The retaining means may consist of a plurality of O-rings. The sealing cap and O-rings may be made from silicon rubber and the cone may be made from plastic. The arms may be made from stainless steel and are attached to the cone using an epoxy adhesive. The ends of the arms may be bent such that the ends of the arms are parallel to the surface through which the cannula will be inserted and the thread retaining means may be located along this portion of the arms.

Figure 1A:
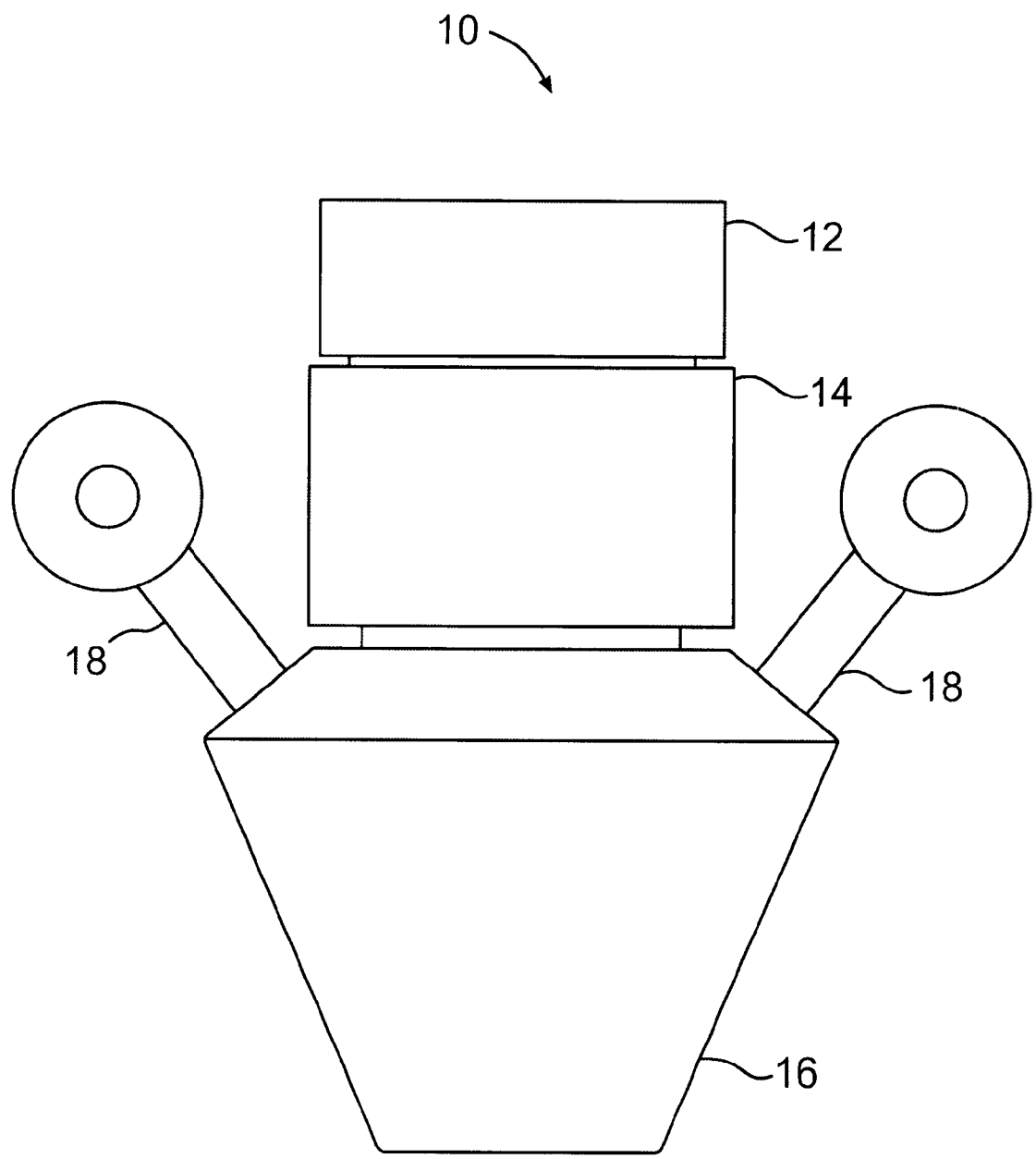
FIG. 1a is a front view of the assembled preferred embodiment.

LIST OF ELEMENTS 10 port
12 sealing cap
14 threaded cone top
16 cone
18 arms
20 sealing cap protuberances
22 opening in sealing cap
24 threaded cone top indentations
26 dashed lines indicating inner surface of threaded cone top
28 notches in top portion of cone
30 O-rings
32 cannula
34 body cavity wall
36 sutures
38 directional arrow

DETAILED DESCRIPTION OF THE PREFERRED EMBODIMENT

Figure 1B:
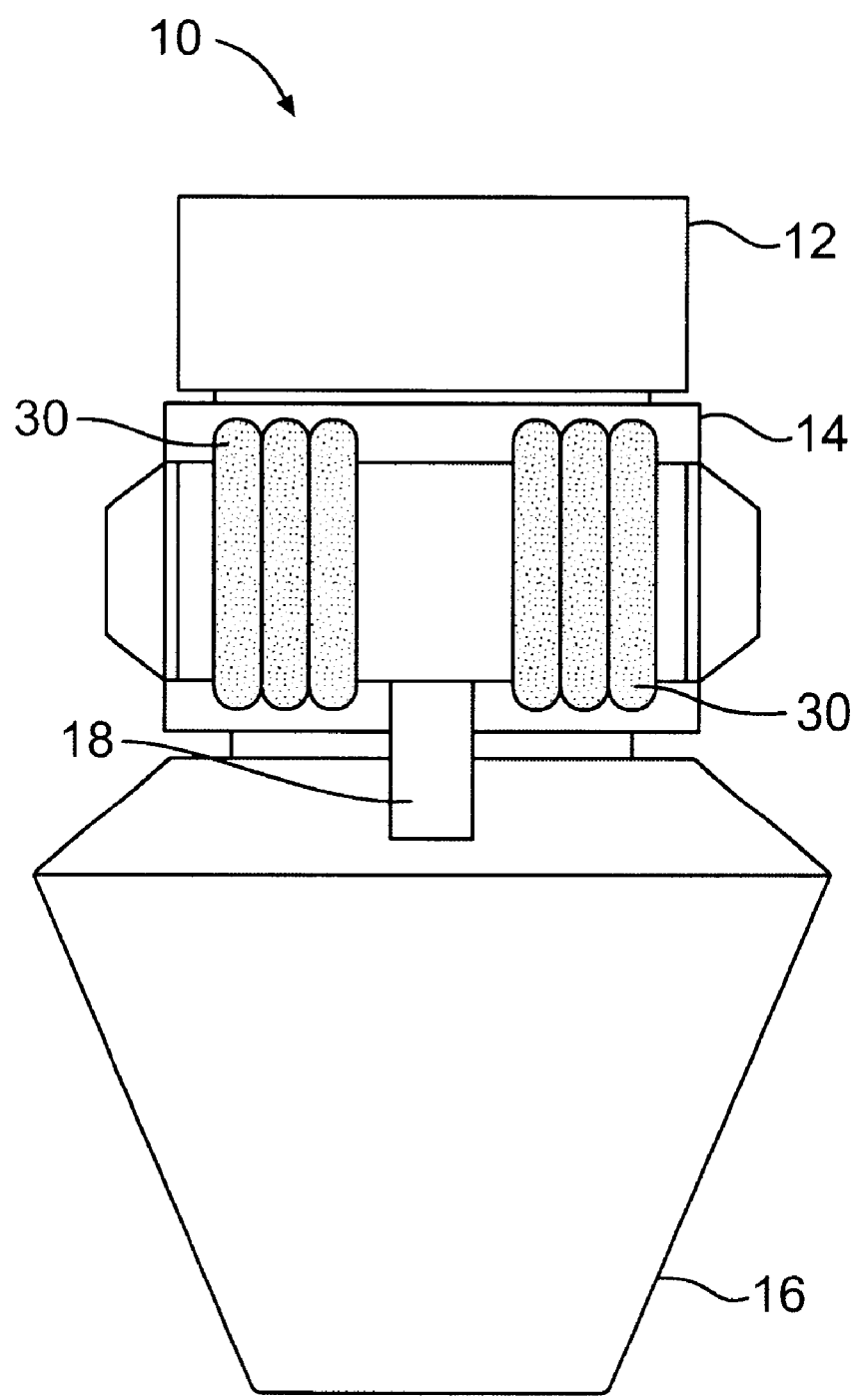
FIG. 1b is a side view of the assembled preferred embodiment.
Figure 2:
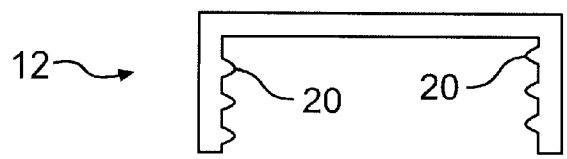
FIG. 2 is a cross sectional view of the sealing cap of the preferred embodiment of the present invention.
Figure 3:
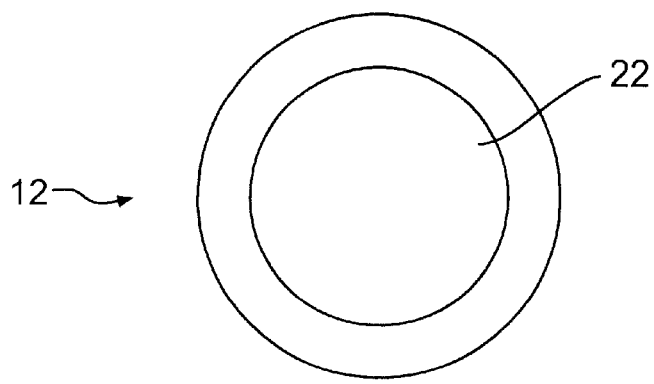
FIG. 3 is a top view of the sealing cap.

FIGS. 1a and 1b show a cannula port 10 according to the present invention. The port 10 consists of a sealing cap 12, a threaded cone top 14, a cone 16 and a pair of arms 18 extending from the cone 16. The sealing cap 12 may be made from silicon rubber and is releasably attached to the threaded cone top 14. The sealing cap 12 preferably includes a system for retaining the sealing cap on the cone top 14 until removal is required. One possible system is a series of protuberances 20 on the sealing cap 12 which mesh with indentations 24 (shown in FIG. 4) on the outside of the cone top 14 as shown in FIG. 2. The sealing cap 12 also includes an opening 22 for accepting a cannula (cannula not shown). This opening 22 is preferably slightly smaller than the diameter of the cannula so that a snug seal between the port 10 and the cannula is provided.

Figure 4:
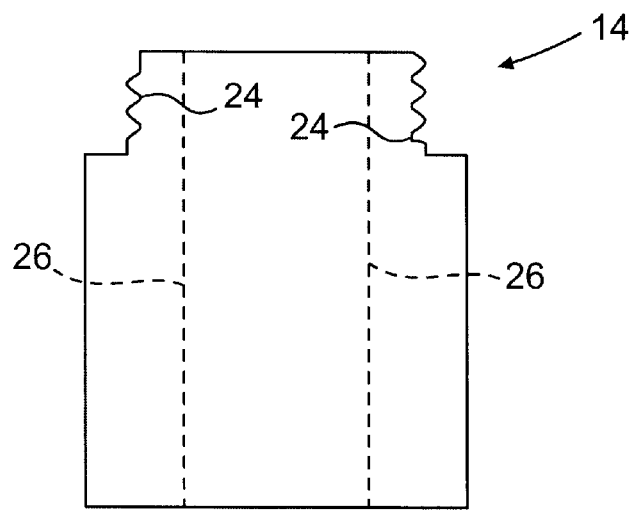
FIG. 4 is a side view of the threaded cone top in the preferred embodiment of the present invention.

The threaded cone top 14 shown in FIG. 4 may be made from a plastic such as Radel plastic. The top portion of the threaded cone top 14 may include indentations 24 for accepting protuberances 20 on the sealing cap 12 in order to retain the sealing cap 12 on the threaded cone top 14. The threaded cone top 14 is hollow to accept a cannula as shown by dashed lines 26. These dashed lines 26 are angled slightly inwards towards the top portion of the threaded cone top 14. The internal surface of the bottom of the threaded cone top 14 is threaded to accept the threaded top portion of the cone 16.

Figure 5:
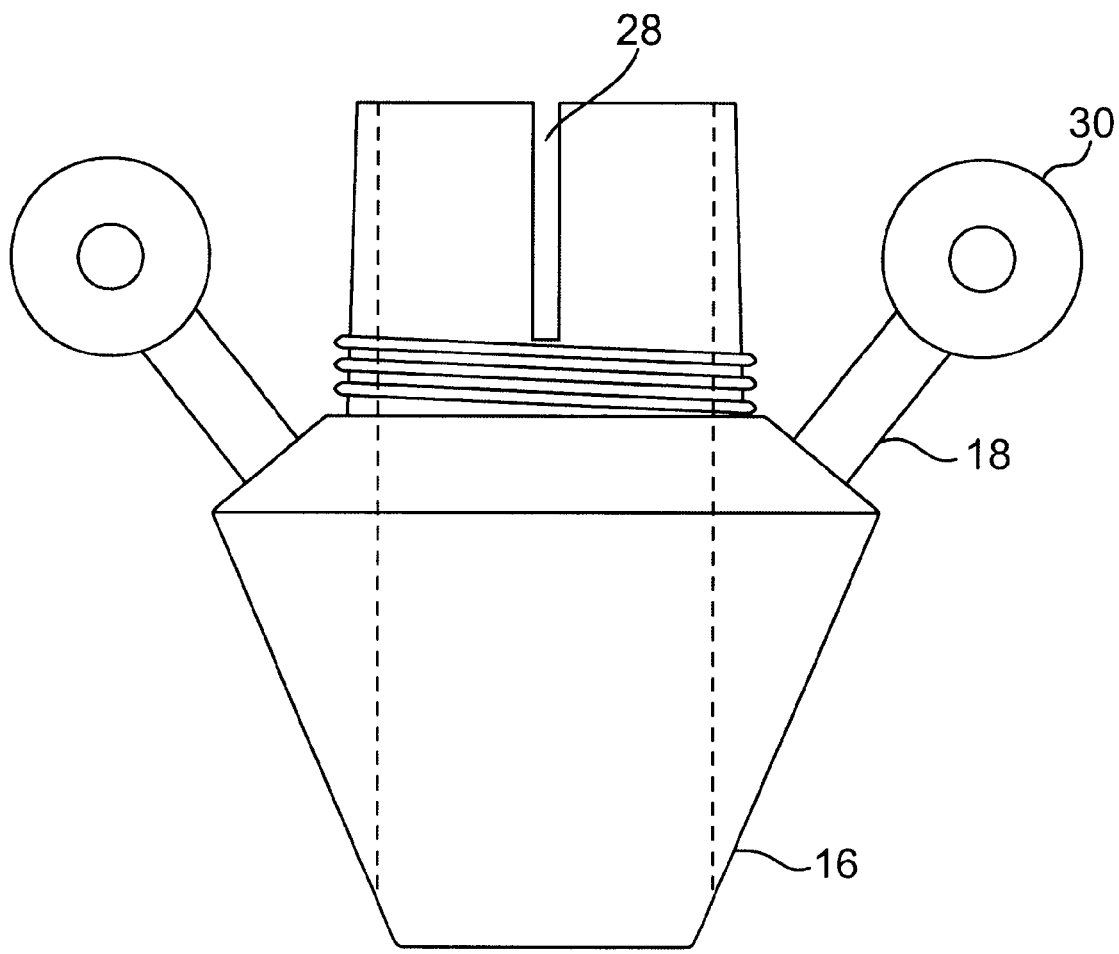
FIG. 5 is a side view of the cone of the preferred embodiment of the present invention.
Figure 7:
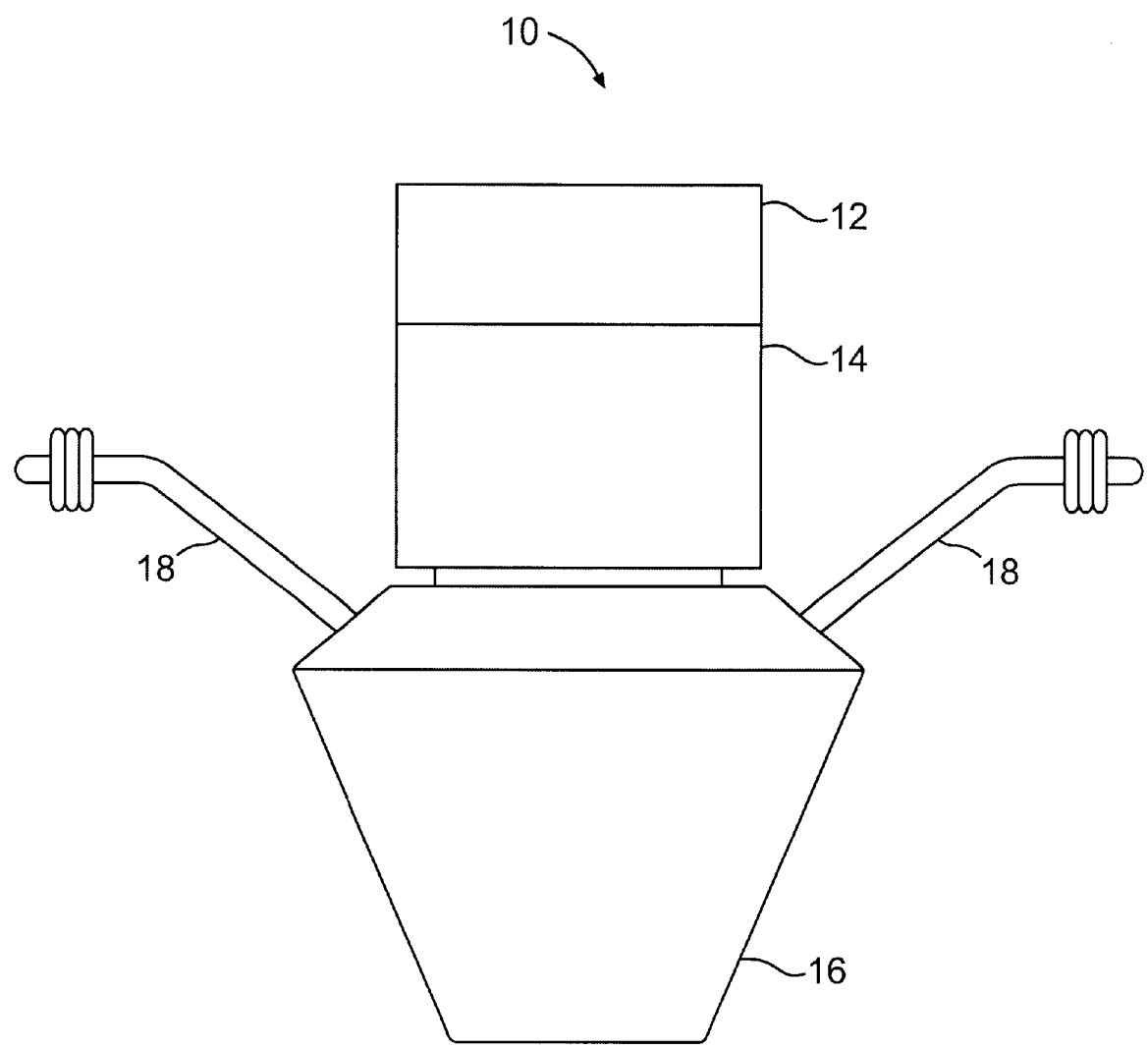
FIG. 7 is a front view of an assembled alternate embodiment.

The cone 16 shown in FIG. 5 may be made from a plastic such as Radel plastic. The top portion of the cone 16 includes a plurality of notches 28 (only one shown) located about the perimeter of the top portion of the cone 16. Below the notches 28, the cone 16 is threaded for accepting the bottom of the threaded cone top 14. The diameter of the top portion of the cone 16 is slightly larger than the diameter of the cannula to be inserted into the port 16 such that the cannula slides easily into the port 16. Extending from the cone are arms 18. The arms 18 may be made from stainless steel and may be affixed to the cone 16 using an epoxy adhesive. A system for retaining sutures is located toward the ends of the arms 18 most distant from the cone 16. In the preferred embodiment, the arms 18 are T-shaped and each arm end includes three silicon rubber O-rings 30 for retaining sutures. In an alternate embodiment shown in FIG. 7, the arms 18 extend from the cone diagonally and the terminal portion of each arm 18 is bent to be parallel with the horizontal. Three silicon rubber O-rings 30 on the bent portion are used to retain sutures.

Figure 6:
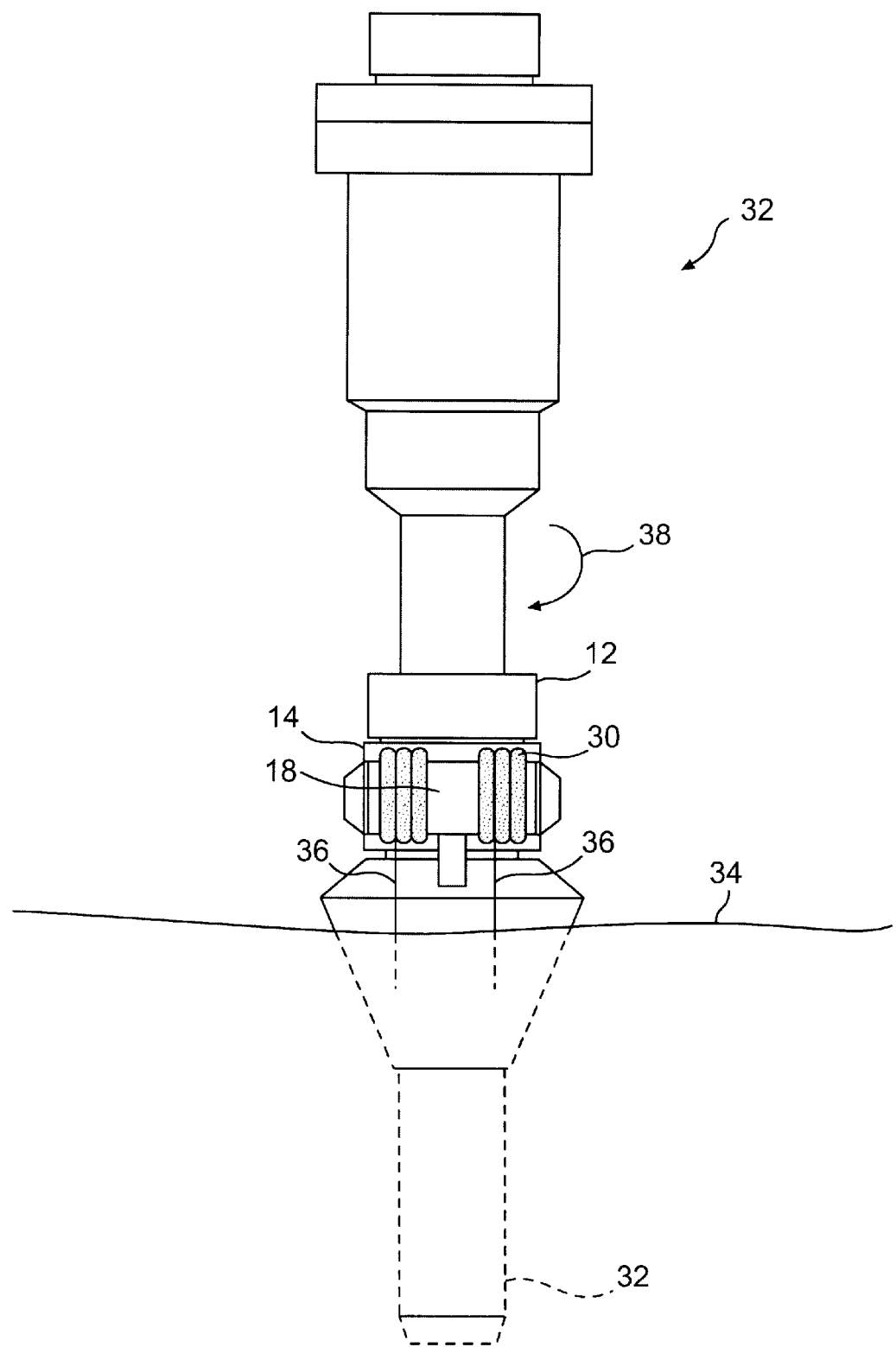
FIG. 6 is a perspective view showing the preferred embodiment in use.

FIG. 6 shows the preferred embodiment of the present invention in use. A cannula 32 is inserted into the port 10 and positioned with the port 10 at the desired height. The port 10 is fixed in place by holding the cone 16 steady and turning the threaded cone top 14 in the direction indicated by the arrow 38. As discussed previously, the internal surface of the threaded cone top 14 is tapered such that the internal diameter at the top of the threaded cone top 14 is less than the internal diameter at the bottom of the threaded cone top 14. As the threaded cone top 14 is screwed onto the cone 16, the notched portion of the cone 16 is forced inward against the cannula 32 by the decreasing diameter of the threaded cone top 14, providing a secure attachment of the port 10 to the cannula 32.

Prior to inserting the cannula 32, sutures 36 are applied through the fascia layer. The cannula 32 is then inserted into the body cavity to be operated on through the body cavity wall 34. The suture thread 36 is then brought up around the O-rings 30 on one side of the T-shaped portion of the arm 18 and pulled snugly so that it is pulled in between the first two O-rings and wrapped again between the second and third O-rings and held in place. Another suture 36 extends through the body cavity wall 34 and is brought up around the O-rings 30 on the other side of the T-shaped portion of the arm 18 and pulled snugly in between the first and second O-rings 30 and wrapped around again in between the second and third O-rings. This process is repeated on both sides of the T-shaped portion of the other arm 18. The depth of the cannula 32 in the body cavity can then be adjusted by loosening the threaded cone top 14, adjusting the cannula 32 and then tightening the threaded cone top 14. This procedure ensures that the cannula 32/port 10 assembly is held in place for the duration of the surgery.

Many improvements, modifications, and additions will be apparent to the skilled artisan without departing from the spirit and scope of the present invention as described herein and defined in the following claims.

What is claimed is:

1. A port comprising:

a sealing cap removably attached to a threaded cone top;

a cone having an upper threaded section for receiving the threaded cone top and a lower conical section; and a pair of arms extending from the cone, each arm including a means for retaining a thread.

2. A port according to claim 1 wherein the cone further comprises an upper segmented section having a plurality of vertical segments, each of which is forced inward upon threading of the cone top onto the cone.

3. A port according to claim 1 wherein the retaining means is a plurality of O-rings.

4. A port according to claim 1 wherein the sealing cap is made from silicon rubber.

5. A port according to claim 3 wherein the O-rings are made from silicon rubber.

6. A port according to claim 1 wherein the cone is made from plastic.

7. A port according to claim 1 wherein the arms are made from stainless steel.

8. A port according to claim 1 wherein the arms attached to the cone using an epoxy adhesive.

9. A port according to claim 1 wherein the arms are T-shaped such that the end portions of each arm is substantially parallel to the surface into which the cannula will be placed.

10. A port according to claim 9 wherein the thread retaining means is located on the end portion of each arm.

11. A port according to claim 1 wherein the arms are bent such that the end portions of the arms are substantially parallel to the surface into which the cannula will be placed.

12. A port according to claim 11 wherein the thread retaining means is located on the end portion of each arm.

* * * * *